United States Patent [19]

Peacock

[11] Patent Number: 5,760,052

[45] Date of Patent: Jun. 2, 1998

[54] COMPOSITION FOR USE AS A FUNGISTAT AND FOR THE TREATMENT OF FUNGAL INFECTIONS

[76] Inventor: Robert Peacock, 2996 Millville-Shandon Rd., Hamilton, Ohio 45013

[21] Appl. No.: 798,030

[22] Filed: Feb. 6, 1997

[51] Int. Cl.$^6$ .......................... A61K 31/44; A61K 31/13
[52] U.S. Cl. ............................... 514/297; 514/641
[58] Field of Search ......................... 514/297, 641

[56] References Cited

U.S. PATENT DOCUMENTS

| 1,614,281 | 1/1927 | Churchman | 514/641 |
|---|---|---|---|
| 1,947,320 | 2/1934 | Truffaut et al. | 514/297 |
| 2,511,838 | 6/1950 | Folsome et al. | 514/297 |
| 4,315,001 | 2/1982 | Blough . | |
| 4,603,122 | 7/1986 | Blough . | |
| 5,357,636 | 10/1994 | Dresdner, Jr. et al. . | |
| 5,547,541 | 8/1996 | Hansen et al. . | |
| 5,547,745 | 8/1996 | Hansen et al. . | |

OTHER PUBLICATIONS

Diogenenes Abstract, Record No. 4004028, "Ribicide Liquid" May 1942.

Diogenese Abstract, Record No. 4002511, "Dymixal Jel" Apr. 1941.

Goodman and Gilman's "The Pharmacological Basis of Therapeutics", 6th ed. pp. 979-980, 1980.

*Primary Examiner*—Raymond Henley, III
*Attorney, Agent, or Firm*—Pepper Hamilton LLP

[57] ABSTRACT

A composition for use as a fungistat for the treatment and prevention of infections such as sporotrichosis, onychomycosis infections, white line disease, hoof rot, jungle rot, pseudallecheria boydii, scopulariopsis, athletes foot, canker sole and fungal infections generally. The fungistat composition includes acriflavine and gentian violet.

12 Claims, No Drawings

COMPOSITION FOR USE AS A FUNGISTAT AND FOR THE TREATMENT OF FUNGAL INFECTIONS

TECHNICAL FIELD

The present invention relates to a composition for, use as a fungistat to prevent infections such as sporotrichosis, onychomycosis, white line disease, hoof rot, jungle rot, canker sole, pseudallecheria boydii, scopulariopsis and fungal infections generally. The composition includes acriflavine and gentian violet.

BACKGROUND ART

Some known uses of acriflavine are set forth below. U.S. Pat. Nos. 4,315,001 and 4,603,122 disclose a treatment of genital and labial herpes infections using photodynamic and intercalating agents such as acriflavine or proflavine followed by white visible light.

U.S. Pat. Nos. 5,547,541 and 5,547,745 disclose that acriflavine is known as an anti-infective and that gentian violet is known as a topical anti-infective.

U.S. Pat. No. 5,357,636 claims a flexible protective medical glove which includes acrif lavine as an antiseptic.

U.S. Pat. No. 4,331,660 discloses a fish fungicide. The patent discloses that acriflavine is a known fungicide. This patent does not disclose a fungistat use of acriflavine.

The Merck Index, Eleventh Edition (1989) discloses at abstract 118 that acriflavine is known as an antiseptic and has veterinary therapeutic applications such as the use in trichomoniases of bulls.

Merck Index, Eleventh Edition (1989), Abstract 4287, discloses that gentian violet is known as a topical anti-infective and has veterinary applications as a topical antimicrobial.

Other known fungicides include, imidazole, clotrimazole, econazole, ketoconazole, ciclopirox olamine, miconazole and naftifine hydrochloride.

There is a need in the art for alternative treatments for onychomycosis, and for effective fungistat compositions. The present invention overcomes the deficiencies of prior art compositions and provides treatments for onychomycosis, etc. and effective fungistat compositions.

DISCLOSURE OF THE INVENTION

The present invention provides for a composition comprising a fungistat effective amount of acriflavine and gentian violet. This product will be sold under the trademark FUNGIDYE.

In another embodiment, the invention provides a method of prevention of fungal infections selected from the group consisting of sportacoccus, onychomycosis, white line disease, jungle rot, canker sole and hoof rot comprising administering a fungistatic effective amount of a composition comprising acriflavine and gentian violet.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

The composition of the invention includes acriflavine and gentian violet. The composition is advantageously used as a fungistat. The term fungistat as used in this specification means an agent that inhibits the growth of fungi. The composition is contrasted with a fungicide which is an agent which kills fungi and their spores. The strong fungicidal use of such compounds causes tissue damage to the skin which provides a further food supply for fungal growth. Applicant has unexpectedly found that fungistatic dosages do not cause tissue damage and thus clear fungal infections and avoids further recurrence.

The composition may be used on and in nail holes of horses or other animal hooves and in fungal infected areas or in areas in which there is a potential for fungal infection. When used on the hoof of an animal, the composition penetrates the hoof wall into all infected cavities. It is insoluble in water or urine. The compositions are compatible with adhesives and yet neutralize and stabilize anti-fungal growth. The composition stops the growth of fungi by eliminating its food supply of dead and damaged tissue.

Advantageously, the composition is used as a fungistat. Contrary to known fungicidal uses of acriflavine, advantageously and unexpectedly, the lower dosage will not kill or harm normal tissue, as fungicidal doses commonly do.

In a preferred embodiment, the composition of the invention comprises the combination of eight grains of acriflavine HCL or acriflavine natural with eight grains of gentian violet mixed in a gallon of water. The composition may optionally include alcohol.

The composition may be used as a fungistat to prevent sportacoccus and onychomycosis infections. Onychomycosis is a fungal disease which often affects the fingernails of bartenders who are exposed to yeast cultures. The composition may also be used for the treatment of white line disease, hoof rot, jungle rot, canker sole and fungal infections generally. The composition may be used in a transdermal formulation.

The composition is also useful as a wound healing agent and as an antiseptic. The composition is useful as a topical treatment or under patch repair for horses hooves. The fungistat composition advantageously, does not contain formaldehyde or copper sulfate.

The acriflavine in the composition may be selected from acriflavine HCL and acriflavine natural. In a preferred embodiment the effective amount of acriflavine is about 0.01 grams to 16 grams and the effective amount of gentian violet is about 0.01 grams to 16 grams.

The composition may further comprise a pharmaceutically acceptable carrier. In a preferred embodiment the pharmaceutically acceptable carrier is selected from distilled water and alcohol. In another embodiment the composition is formulated for transdermal delivery. In still another embodiment the composition is formulated as a cream. The composition is formulated for topical delivery.

In a preferred embodiment, 8 grains or 8 tablets of acriflavine and 4 grain or 8 grains of gentian violet are mixed into one half gallon of distilled water. In an alternative embodiment, 64 grains acriflavine and 64 grains of gentian violet mixed with distilled water makes 16 gallons of the composition.

The compositions the present invention are useful in pharmaceutical compositions for topical delivery. Topical application can be in the form of ointments, creams, lotions, jellies and sprays. The pharmaceutical compositions (wt %)

of the active ingredient with a carrier or vehicle in the composition in about 1 to 99% and preferably about 5 to 15%.

A preferred use of the compounds according to the invention is as topical agent suitable for application to skin, nails or hoofs. Another preferred use of the compounds is in a transdermal pharmaceutical preparation, which is particularly useful in the treatment of onychomycosis in man. The compositions may be administered transdermally and, if desired a more concentrated slow release form may be administered. Accordingly, incorporation of the active compounds in a slow release matrix may be implemented for administering transdermally. The compounds may be administered transdermally at about 1 to 99% of the composition and preferably about 0.61 grams per lb of carrier of the active ingredient in the vehicle or carrier.

Transdermal therapeutic systems are self-contained dosage forms that, when applied to intact skin or hoof, deliver drug(s) at a controlled rate to the systemic circulation. Advantages of using the transdermal routing include: enhanced therapeutic efficacy, reduction in the frequency of dosing, reduction of side effects due to optimization of the blood-concentration versus time profile, increased patient compliance due to elimination of multiple dosing schedules, bypassing the hepatic "first-pass" metabolism, and providing a predictable and extended duration of activity. However, the main function of the skin is to act as a barrier to entering compounds. As a consequence, transdermal therapy has so far been restricted to a limited number of drugs that possess the desirable physicochemical properties for diffusion across the skin barrier. One effective method of overcoming the barrier function of the skin is to include a penetration enhancer in the formulation of a transdermal therapeutic system. See Barry, Brian W.: *Dermatological Formulations: Percutaneous Absorption* (Dekker, New York, 1983); Bronough et al, *Percutaneous Absorption, Mechanisms-Methodology-DrugDelivery*, (Marcel Dekker, New York, N.Y. 1985); and Monkhouse et al, Transdermal drug deliver-problems and promises. *Drug Dev. Ind. Pharm.*, 14, 183–209 (1988).

A penetration enhancer is a chemical compound that, when included in a formulation, temporarily increases the permeability of the skin to a drug allowing more of the drug to be absorbed in a shorter period of time. Several different types of penetration enhancers have been reported such as dimethylsulfoxide, n-decyl methyl sulfoxide, N,N-dimethylacetamide, N<Ni-dimethylformamide, 1-dodecylazacycloheptan-2-one (Azone), propylene glycol, ethanol, pyrrolidones such as N-methyl-2-pyrrolidone (NMP) and surfactants. See Bronough et al, supra, and Stoughton et al, Azone: a New Non-toxic enhancer of percutaneous penetration. *Drug Dev. Inc. Pharm.*, 9, 725–744 (1983).

N-methyl-2-pyrrolidone is a versatile solvent which is miscible with water, ethyl alcohol, ether, chloroform, benzene, ethyl acetate and carbon disulfide. N-methylpyrrolidone has been widely used as a solvent in industrial processes such as petroleum refining, GAF Corp.: "M-Pyrol (N-methyl-2-pyrrolidone) Handbook.", GAF Corp., New York, 1972. It is currently used as a solubilizing agent in topical and parenteral veterinary pharmaceuticals and is now under consideration for use in products intended for humans, Wells, D. A. et al: Disposition and Metabolism of Double-Labeled [$^3$H and $^{14}$C] N-methyl-2-pyrrolidone in the Rat. *Drug Met. Disps.*, 16, 243–249 (1988). N-methylpyrrolidone has also been shown to be an effective penetration enhancer. Barry et al, Optimization and Bioavailability of Topical Steroids: Penetration Enhancers Under Occlusion. *J. Inv. Derm.*, 82, 49–52 (1984); Akter et al, Absorption Through human Skin of Ibuprofen and Flurbiprofen; Effect of Dose Variation, Deposited Drug Films, Occlusion and the Penetration Enhancer N-methyl-2-pyrrolidone. *J. Pharm. Pharmacol.*, 37, 27–37 (1984); Holegaard et al, Vesical Effect on Topical Drug Delivery IV. Effect of N-methylpyrrolidone and Polar Lipids on Percutaneous Transport. *Int. J. Pharm.*, 43, 233–240 (1988); Sugibayashi et al, Effect of Several Penetration Enhancers on the Percutaneous Absorption of Indomethacin in Hairless Rat. *Chem. Pharm. Bull.*, 36, 1519–1529 (1988); Bennett et al, Optimization of Bioavailability of Topical Steroids: Nonoccluded penetration Enhancers Under Thermodynamic Control. *J. Pharm. Pharmacol.*, 37, 298–304 (1985); Sasaki et al, Enhancing Effect of Pyrrolidone Derivatives on Transdermal Drug Delivery. 1. *Ing. J. Pharm.*, 44, 14–24 (1988); lee et al, Toxicity of N-methyl-2-pyrrolidone (NMP): Teratogenic, Subchronic and Two-year Inhalation Studies, *Fund. Appl., Tox.*, 9, 222–235 (1987).

The above compositions of the invention may be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinyl pyrrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a composition according to the present invention is about 0.01 to 16 grams and is preferably administered from 1 to 3 times daily. In an alternative embodiment of the invention the drug composition is administered at least once a day. This dosage is effective for all fungistat treatment uses.

Additional topical formulations are known in the art such as disclosed in *Remingtons Pharmaceutical Sciences*, 18th Ed. 1990, Mack Publishing Co., Chapter 87 entitled "Medical Applications" which discloses formulations for creams, ointments, transdermals, dressings, and plasters (incorporated herein by reference in its entirety).

The composition of the invention may be administered to cuts and bruises on animals to prevent fungal infection and allow for quick healing.

In a preferred embodiment of the invention the composition is administered along with the oral vitamin supplement sold under the trademark NUFOOT. This is a vitamin supplement which bolsters the immune system and assists in the avoidance of recurrence of fungal infections. Any known immune system stimulating drug may be administered with the composition of the invention.

The following non-limiting examples reflect several applications of the present invention.

EXAMPLE 1

8 grains of acriflavine natural (also known as acriflavine neutral) purchased from Rudell Drug and Chemical Co. Inc, Irvington, N.J. 07111 [CAS-8048-52-0; NDC 17317-000-82] and 8 grains of gentian violet Rudell Drug and Chemical Co. Inc, Irvington, N.J. 07111 [CAS 548-62-9; NDC 17317-0183-2] are mixed in one gallon of distilled water. The mixture is administered to horses hooves twice daily for one to six weeks. After one to six weeks the white line disease is gone. Continued use prevents recurrence of fungal infections.

EXAMPLE 2

10 grains of acriflavine HCL purchased from Rudell Drug and Chemical Co. Inc, Irvington, N.J. 07111 [CAS-8063-24-9; NDC 17317-08-07-3] and 10 grains of gentian violet are mixed in one gallon of distilled water. The mixture is administered to horses hooves twice daily for one week. After four weeks the hoof rot infections are gone. Continued use prevents recurrence of fungal infections.

EXAMPLE 3

4 grains of acriflavine and 4 grains of gentian violet are mixed into a cream formulation. The mixture is administered to human finger nails twice daily for one week. After six weeks the sporotrichosis or onychomycosis infections are gone. Continued use prevents recurrence of fungal infections.

EXAMPLE 4

16 grains of acriflavine and 16 grains of gentian violet are mixed into a cream formulation. The mixture is administered to humans with athletes foot twice daily for one week. After one week the athletes foot infection is clear. Continued use prevents recurrence of fungal infections.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

I claim:

1. A composition comprising acriflavine and gentian violet, wherein said acriflavine and gentian violet are present at a concentration of 0.13% by weight or less.

2. The composition of claim 1 wherein said acriflavine is selected from acriflavine HCL and acriflavine natural.

3. The composition of claim 1, wherein in said effective amount of acriflavine is about 0.01 grams to 16 grams.

4. The composition of claim 1, wherein in said effective amount of gentian violet is about 0.01 grams to 16 grams.

5. The composition of claim 1, wherein said composition further comprises a pharmaceutically acceptable carrier.

6. The composition of claim 1, wherein said pharmaceutically acceptable carrier is selected from distilled water and alcohol.

7. The composition of claim 1, wherein said composition is formulated for transdermal delivery.

8. The composition of claim 1, wherein said composition is formulated as a cream.

9. The composition of claim 1, wherein said composition is formulated for topical delivery.

10. A method of prevention of fungal infections comprising the step of administering a composition comprising acriflavine and gentian violet, wherein said acriflavine and gentian violet are present at a concentration of 0.13% by weight or less.

11. A method of treatment of athletes foot comprising the step of administering a composition comprising acriflavine and gentian violet, wherein said acriflavine and gentian violet are present at a concentration of 0.13% by weight or less.

12. A method of prevention of fungal infections according to claim 10 wherein said fungal infection is selected from the group consisting of sportacoccus, onychomycosis infections, white line disease, hoof rot, jungle rot, athletes foot, pseudallecheria boydii, scopulariopsis and canker sole.

* * * * *